United States Patent [19]
Arnold et al.

[11] 4,131,748
[45] Dec. 26, 1978

[54] p-TERPHENYLENE-DICARBOXYLIC ACIDS AND THEIR SYNTHESIS

[75] Inventors: Fred E. Arnold, Centerville, Ohio; James F. Wolfe, Menlo Park, Calif.

[73] Assignee: The United States of America as represented by the Secretary of the Air Force, Washington, D.C.

[21] Appl. No.: 811,346

[22] Filed: Jun. 29, 1977

[51] Int. Cl.$^2$ .................. C07C 63/33; C08F 18/14
[52] U.S. Cl. .................. 562/488; 260/332.2 A; 260/347.3; 528/183; 562/427; 562/466; 544/353; 546/264; 546/267; 546/283; 546/284; 546/330; 546/342

[58] Field of Search .............. 260/515 P, 515 M, 516, 260/520 R

[56] References Cited
U.S. PATENT DOCUMENTS

| 3,903,101 | 9/1975 | Yoshida et al. | 260/515 P |
|---|---|---|---|
| 3,953,498 | 4/1976 | Hartle | 260/515 P |

Primary Examiner—James O. Thomas, Jr.
Assistant Examiner—G. T. Breitenstein
Attorney, Agent, or Firm—Joseph E. Rusz; Cedric H. Kuhn

[57] ABSTRACT p-Terphenylene-dicarboxylic acids in which aromatic groups are attached to the middle phenyl group of the terphenylene moiety. The compounds are useful as monomers in the preparation of rod-like, para-ordered aromatic heterocyclic polymers.

7 Claims, No Drawings p-TERPHENYLENE-DICARBOXYLIC ACIDS AND THEIR SYNTHESIS

RIGHTS OF THE GOVERNMENT

The invention described herein may be manufactured and used by or for the Government of the United States for all governmental purposes without the payment of any royalty.

FIELD OF THE INVENTION

This invention relates to p-terphenylene-dicarboxylic acids having pendant aromatic groups and to a process for their synthesis.

BACKGROUND OF THE INVENTION

In U.S. Pat. No. 3,671,542, it is disclosed that high strength, high modulus fibers can be obtained by the spinning of concentrated solutions of rigid chain, rod-like polyamides. The molecular geometry of the polymers must be such as to define a straight line chain conformation, thereby generating anistropic, liquid crystalline solutions. The success or failure of obtaining such solutions is to a large degree dependent on the variety of solvents which can be used as well as temperature, percent concentration, molecular weight, and molecular weight distribution. As disclosed in the aforementioned patent, strong acids are used as solvents, which is a disadvantage from a processing standpoint. Also, the polyamides are hydrolytically unstable, a condition which renders the polymers unsuitable for many applications.

It is a principal object of this invention, therefore, to provide p-terphenylene-dicarboxylic acid monomers which can be used in the preparation of hydrolytically and thermally stable rod-like polymers.

Another object of the invention is to provide monomeric materials containing pendant aromatic groups which prevent the close packing of chains when the materials are polymerized, thereby reducing the high degree of intramolecular association and, as a result improving solubility parameters.

A further object of the invention is to provide a process for synthesizing the p-terphenylene-dicarboxylic acid monomers.

Other objects and advantages of the invention will become apparent to those skilled in the art upon consideration of the accompanying disclosure.

SUMMARY OF THE INVENTION

The present invention resides in a p-terphenylene-dicarboxylic acid having the following formula:

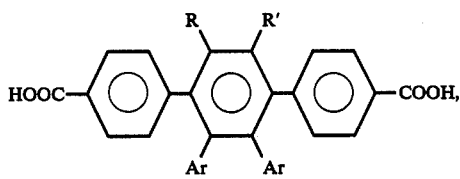

(I)

wherein Ar is a monovalent aromatic radical, and R and R' are individually selected from the group consisting of hydrogen, a monovalent aromatic radical, a monovalent aliphatic radical, a monovalent cycloaliphatic radical and a monovalent heterocyclic radical. Examples of monovalent aromatic radicals include the following:

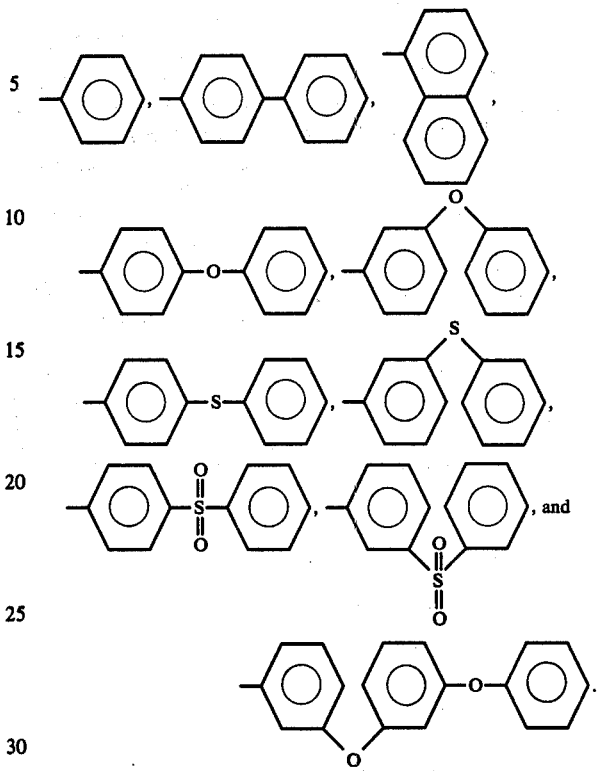

The following are examples of monovalent aliphatic, cycloaliphatic and heterocyclic radicals: $-CH_2-CH_3$, $-CH_2-CH_2-CH_3$, $-CH_2-CH_2-CH_2-CH_3$,

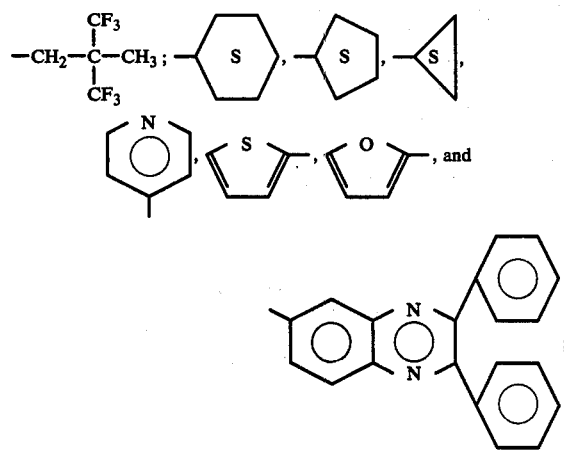

When monomers as defined by the foregoing formula undergo a condensation reaction with a suitable comonomer, the pendant aromatic groups prevent close packing of polymer chains. Intermolecular associations are thereby reduced so that solubility parameters are improved. As a result the polymers are rendered more processable, thereby alleviating the problem of intractability of conventional aromatic polymers. In particular, the "para" geometry of the monomers is such as to generate rod-like polymers when polymerized with para-ordered comonomers, which provides diversity in the dissolution of such rod-like systems.

The monomeric materials of this invention can be polymerized with conventional comonomers so as to prepare amide, esters, benzimidazo, and benzithiozole polymers. The monomers are especially useful in preparing benzobisoxazole polymers by polycondensation with multifunctional ortho amino phenols, such as 4,6-diaminoresorcinol, as disclosed in our copending U.S. application Ser. No. 811,345, filed on June 29, 1977, now U.S. Pat. No. 4,108,835. The disclosure of this copending application is incorporated herein by reference.

One embodiment of the present invention is concerned with a process for synthesizing p-terphenylene-dicarboxylic acids of Formula I in which at least one of the R and R' groups in other than hydrogen. In conducting this process, a four-stage procedure is followed in which the reactions involved are illustrated by the following equations

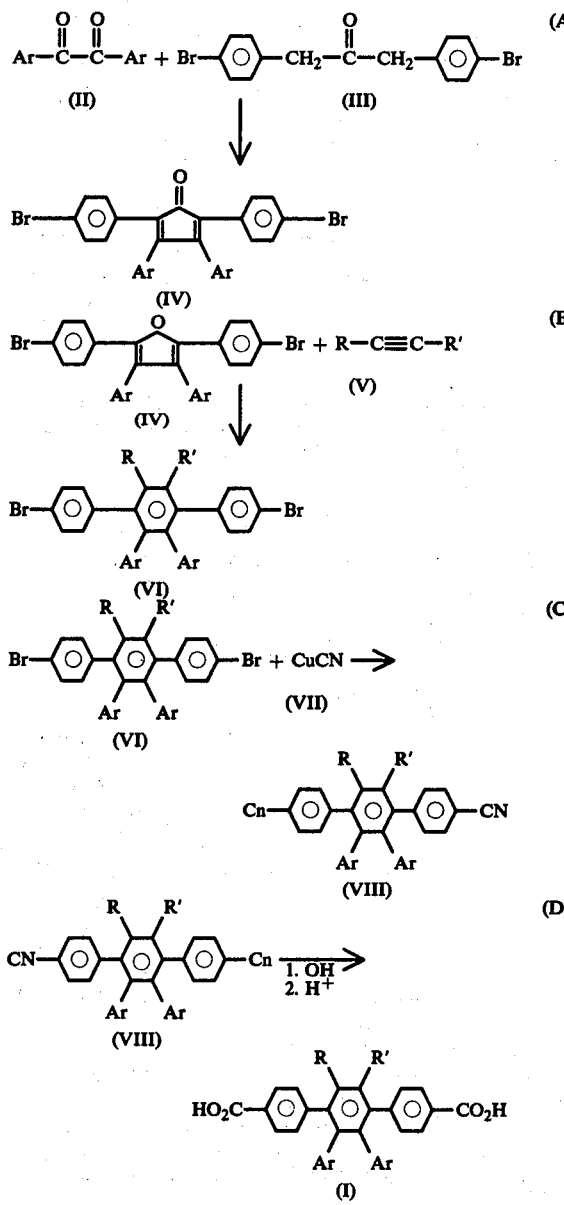

As shown by equation (A), an aromatic benzil (II) is reacted with 1,3-bis(p-bromophenyl)-2-propanone (III) to form 2,5-bis(p-bromophenyl)-3,4-diarylcyclopentadienone (IV). Substantially equimolar amounts of compounds (II) and (III) are utilized, and the reaction is carried out in the presence of an alkali metal hydroxide under reflux conditions in a suitable reaction medium. An alcohol, such as ethanol, can be conveniently used as the reaction medium. The amount of alkali metal hydroxide can vary within rather broad limits but generally ranges from about 0.1 to 0.75 mole per mole of the aromatic benzil. The reaction mixture is usually maintained under reflux conditions for a period ranging from about 15 minutes to one hour.

In the second stage of the process as shown by equation (B), compound (IV) prepared in the first stage is reacted with an acetylene compound (V) to form dibromo terphenyl compound (VI). It is noted that no more than one of the R and R' radicals of compound (V) can by hydrogen. In conducting the reaction, a molar excess of the acetylenic compound is used, e.g., 1.5 to 10 moles per mole of compound (IV). The reaction is carried out in a suitable reaction medium, such as a chlorinated hydrocarbon, under reflux conditions for a period of about 15 minutes to one hour. As indicated by equation (C), the third stage involves reaction compound (VI) with cuprous cyanide to form dicyano terphenyl compound (VIII). A molar excess of cuprous cyanide, e.g., 1.5 to 3 moles per mole of compound (VI), is utilized. The reaction is conducted in an inert atmosphere under reflux conditions, utilizing a suitable reaction medium, such as N-methyl-2-pyrrolidone. A reaction period of about 8 to 24 hours is usually sufficient to affect the substitution of the bromine atoms with cyano groups. In the fourth and final stage of the process, terphenyl compound (VIII) is hydrolyzed with an inorganic base and then acidified to provide p-terphenylene-dicarboxylic acids (I) of this invention.

When it is desired to synthesize a monomer of this invention (Formula I) in which R and R' are both hydrogen, acetylene is not used in the reaction represented by equation (B). Rather, bicyclo[2,2,1]heptadiene is employed in the Dels-Alder reaction, giving the dibromo terphenyl (VI) with the loss of carbon monoxide and cyclopentadiene. The reaction involved is illustrated by the following equation:

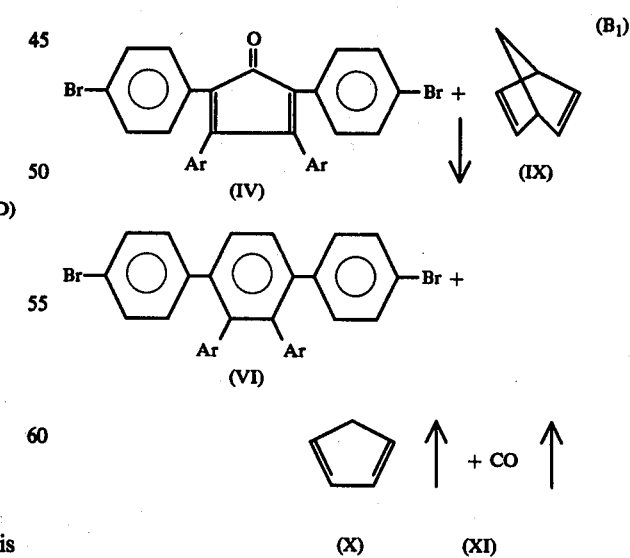

In conducting the reaction shown by equation (B₁), a molar excess of the heptadiene (IX) is reacted with the dibromo cyclopentadienone (IV) prepared as described above (equation A). The reaction is carried out under reflux condition, using a hydrocarbon as the reaction medium. During the reaction period, which usually lasts from 6 to 12 hours, cyclopentadiene (X) and carbon monoxide (XI) are evolved and the dibromo terphenyl compound (VI) is formed. The third and fourth stages of the process as described above are then followed in preparing compounds (I) of this invention in which R and R' are both hydrogen.

As seen from the foregoing, the source of the Ar groups is the benzil compounds (II). Examples of such compounds that can be used include benzil; 4,4'-phenoxybenzil; 3,3'-phenoxybenzil; 4,4'-phenylthiobenzil; 3,3'-phenylthiobenzil; 4,4'-phenylsulfonylbenzil; 3,3'-phenylsulfonylbenzil; and the like. The source of the R and R' groups when no more than one of the groups is hydrogen is the acetylene compounds (V). Examples of suitable acetylene compounds include phenylacetylene, naphthylacetylene, diphenylacetylene, dinaphthylacetylene, 4-phenoxyacetylene, 4,4'-diphenoxydiphenylacetylene, 3-phenoxyacetylene, 3,3'-diphenoxydiphenylacetylene, 4-phenylthioacetylene, 4-ethynylpyridine, 2-ethynylfuran, 2-ethylnylthiophene, cyclohexylacetylene, n-butylacetylene, n-propylacetylene, isopropylacetylene, and the like. As mentioned above, when R and R' of the compound of Formula (I) are both hydrogen, bicyclo[2,2,1]heptadiene is used instead of acetylene per se.

A more comprehensive understanding of the invention can be obtained by referring to the following illustrative examples which are not intended, however, to be -propanone limitative of the invention.

EXAMPLE I

Preparation of 4,4''-Dicarboxy-2',3',5'-triphenyl-p-terphenyl a. 2,5-Bis(p-bromophenyl)-3,4-diphenylcyclopentadienone: To a refluxing solution of 50 g (136 mmol) of 1,3-bis(p-bromophenyl)-2-propane and 28.5 g (136 mmol) of benzil in 375 ml of absolute ethanol was added dropwise over a period of 5 minutes a solution of 4 g of potassium hydroxide in 100 ml of absolute ethanol. The mixture rapidly turned from a clear yellow to a dark magenta color. Reflux and stirring was maintained for an additional 15 minutes and then the mixture was allowed to stand overnight. The mixture was filtered, washed with 95% ethanol, air dried and recrystallized from pyridine. The yield of purplish black crystals was 61.8 g (83.8%) (mp 249–250° C).

Analysis Calc'd for $C_{29}H_{18}Br_2O$: C, 64.22%; H, 3.34%. Found: C, 64.32%; H, 3.48%.

b. 4.4''-Dibromo-2',3',5'-triphenyl-p-terphenyl: A mixture of 40.0 g (73.8 mmol) of 2,5-bis(p-bromophenyl)-3,4-diphenylcyclopentadienone, 31 g (303 mmol, 33.3 ml) of phenylacetylene and 375 ml of o-dichlorobenzene was heated to reflux. The dark purple solution turned clear yellow within 30 minutes. After an additional 15 minutes, the solution was poured into 2.5 liters of methanol to give 42.4 g (93.2%) of a white precipitate (mp 264° C).

Analysis Calc'd for $C_{36}H_{24}Br_2$: C, 70.15; H, 3.92; Br, 25.92. Found: C, 70.67; H, 4.08; Br, 25.52.

c. 4,4''-Dicyano-2',3',5'-triphenyl-p-terphenyl: To a mixture of 5.2 g (8.4 mmol) of 4,4''-dibromo-2',3',5'-terphenyl-p-terphenylene and 1.74 g (19.4 mmol) of cuprous cyanide was added 51 ml of freshly distilled dry N-methyl-2-pyrrolidone under a stream of dry nitrogen. The mixture was heated under nitrogen to reflux. After 22 hours of reflux, the dark brown mixture was poured while hot into a warm solution of sodium cyanide (40 g) in 120 ml of water to give a gray solid. The material was filtered and washed twice with warm 10% aqueous sodium cyanide and then thoroughly with water to give 3.56 g (83.5%) of product.

Analysis Calc'd for $C_{38}H_{24}N_2$: C, 89.72; H, 4.75. Found: C, 89.32; H, 4.81.

d. 4,4''-Dicarboxy-2',3',5'-triphenyl-p-terphenyl: A mixture of 15 g (25.6 mmol) of 4,4''-dicyano-2',3',5'-triphenyl-p-terphenyl, 46 g of potassium hydroxide and 450 ml of ethylene glycol was maintained at reflux for 20 hours. The resultant clear orange-brown solution was cooled and poured into 1.2 liters of dilute hydrochloric acid to give a tan precipitate. The crude diacid was filtered, dissolved in cold N,N-dimethylacetamide, treated with activated charcoal, heated and filtered. Addition to 1 liter of 3N hydrochloric acid gave a light tan precipitate. The precipitate was dissolved in dilute potassium hydroxide, treated with activated charcoal, heated and filtered. Crystals of the dipotassium salt formed overnight; mp 350° C; ir (MBr) 1390 and 1590 $cm^{-1}(COO^-)$ no carbonyl absorption. The diacid salt was dissolved in hot water filtered through a Celite pad to remove residual charcoal, and dilute hydrochloric acid was added. The yield of white powder was 6.5 g (46%); mp 425° (DSC); ir (MBr) 1670 $cm^{-1}$ (C=O); MS, m/4 546 (M)+, 529 (M+H=H_2O)+, 503 (M+H—CO_2)$^{30}$.

Analysis Calc'd for $C_{38}H_{26}O_4$: C, 83.50; H, 4.79. Found: C, 83.65; H, 4.88.

EXAMPLE II

Preparation of 4,4''-Dicarboxy-2',3'-diphenyl-p-terphenyl a. 4,4'-Dibromo-2',3'-diphenyl-p-terphenyl: A mixture of 60 g (110.6 mmol) of 2,5-bis(p-bromophenyl)-3,4-cyclopentadienone (prepared as described in Example I), 108.6 g (1.18 mol) of bicyclo[2.2.1]heptadiene and 300 ml of toluene was heated to reflux (104° C). After approximately 2 hours the color had noticeably faded, after 3 hours the color was clear pink, and a precipitate had formed after 9 hours. The mixture was cooled and 150 ml of methanol was added. The light pink precipitate was collected by filtration to give 46.5 g (77.8%) of product.

Analysis Calc'd for $C_{30}H_{20}Br_2$: C, 66.68; H, 3.73. Found: C, 65.95; H, 3.95.

b. 4,4''-Dicyano-2',3'-diphenyl-p-terphenyl: To a mixture of 10 g (18.5 mmol) of 4,4'-dibromo-2',3''-diphenyl-p-terphenyl, 3.8 g (42.6 mmol) of cuprous cyanide was added 58 ml of dry N-methyl-2-pyrrolidone under a stream of dry nitrogen. After 10 hours of reflux, the hot, dark brown mixture was poured into a warm solution of sodium cyanide (67 g) in 200 ml of water to give a gray precipitate. The material was worked up as described above except that it was recrystallized twice from benzene (once with the use of charcoal) to afford 4.65 g (58%) of product.

Analysis Calc'd for $C_{32}H_{20}N_2$: C, 90.72; H, 4.23. Found: C, 90.32; H, 4.51.

c. 4,4''-Dicarboxy-2',3'-diphenyl-p-terphenyl: A mixture of 4.6 g of 4,4''-dicyano-2',3'-diphenyl-p-terphenyl, 20 g of potassium hydroxide and 190 ml of ethylene glycol was heated under reflux for 16 hours after which time it was a light orange solution. The solution was cooled slightly and 150 ml of water added. The resultant precipitate was filtered, dissolved in hot water, charcoal was added and the mixture was hot filtered. Dilute hydrochloric acid was added to the filtrate. The diacid was then precipitated from 450 ml of dimethylacetamide with dilute hydrochloric acid after treatment with charcoal to give 4.70 g (94%) of product; mp 425° C (DSC); MS, m/e 470 (M)+, 453 (M+H—H$_2$O)+, 427 (M+H—CO$_2$)+.

Analysis Calc'd for C$_{32}$H$_{22}$O$_4$: C, 81.68; H, 4.72. Found: C, 81.54; H, 4.35.

EXAMPLE III

Preparation of 4,4''-Dicarboxy-2',3',5',6'-tetraphenyl-p-terphenyl a. 4,4''-Dibromo-2',3',5',6'-tetraphenyl-p-terphenyl: A mixture of 15.0 g (27.7 mmol) of 2,5-bis(p-bromophenyl)-3,4-diphenylcyclopentadienone (prepared as described in Example I), 19.7 g (111 mmol) of diphenylacetylene and 140 ml of o-dichlorobenzene was maintained at reflux for 64 hours after which time the purple color had changed to clear brown. The solution was cooled and filtered to give 17.5 g (91%) of product as white platelets.

Analysis Calc'd for C$_{42}$H$_{28}$Br$_2$: C, 72.8; H, 4.1; Br, 23.1. Found: C, 74.4; H, 4.1; Br, 20.8.

b. 4,4''-Dicyano-2',3',5',6'-tetraphenyl-p-terphenyl: To a mixture of 9.95 g (13.7 mmoles) of 4,4'-dibromo-2',3',5',6'-tetraphenyl-p-terphenyl and 2.96 g (33.0 mmoles) of cuprous cyanide was added 85 ml of dry N-methylpyrrolidone under a stream of dry nitrogen. After 10 hours of reflux, the hot, dark brown mixture was poured into a warm solution of sodium cyanide (67 g) in 200 ml of water to give a light gray solid. The material was worked up as described above, except that it was purified by passing it through a column of silica gel with benzene as the eluent to give 5.5 g (65%) of white crystalline product.

Analysis Calc'd for C$_{44}$H$_{28}$N$_2$: C, 90.38; H, 4.83; N, 4.79. Found: C, 90.90; H, 4.93; N, 4.11.

c. 4,4''-Dicarboxy-2',3',5',6'-tetraphenyl-p-terphenyl: A mixture 5.33 g of 4,4''-dicyano-2',3',5',6'-tetraphenyl-p-terphenyl, 19 g of potassium hydroxide and 185 ml of ethylene glycol was heated under reflux for 10 hours. The solution was cooled slightly and 150 ml of water added. The resultant precipitate was isolated by filtration and purified as described above to give 2.60 g (46%) yield of product.

Analysis Calc'd for C$_{44}$H$_{30}$O$_4$: C, 84.87; H, 4.86. Found: C, 84.51; H, 4.45.

As seen from the foregoing, the present invention provides p-terphenylene-dicarboxylic acids in which at least two aromatic groups are attached to the middle phenyl group of the terphenyl moiety. When the compounds are used as monomers with suitable comonomers to prepare rod-like polymers, particularly benzobisoxazole polymers, the presence of the pendant aromatic groups prevents close packing of polymer chains and concomitant reduction of intermolecular associations. The solubility parameters of the polymers are thereby improved, rendering the polymers more processable and, therefore, alleviating the intractability problem of conventional aromatic polymers.

As will be evident to those skilled in the art, modifications of the present invention can be made in view of the foregoing disclosure without departing from the spirit and scope of the invention.

We claim:

1. A p-terphenylene-dicarboxylic acid having the following structural formula:

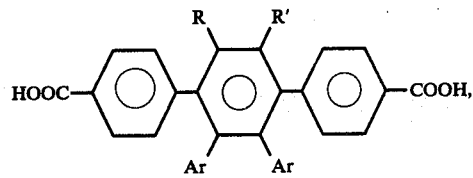

wherein Ar is a monovalent aromatic radical selected from the group consisting of

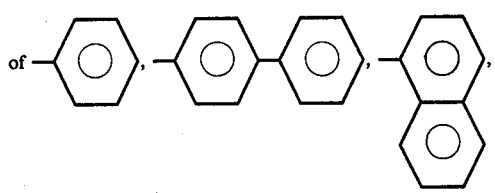

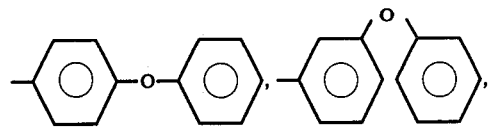

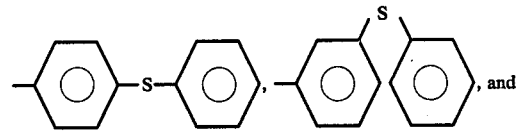

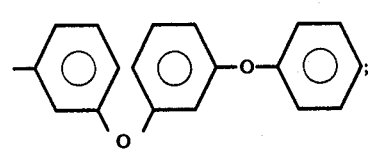

and R and R' are individually selected from the group consisting of hydrogen, a monovalent aromatic radical as listed above, —CH$_2$—CH$_3$, —CH$_2$—CH$_2$—CH$_3$, —CH$_2$—CH$_2$—CH$_2$—CH$_3$,

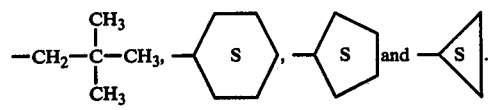

2. The p-terphenylene-dicarboxylic acid according to claim 1 in which Ar is

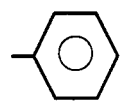

and R and R' are each

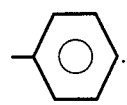

3. The p-terphenylene-dicarboxylic acid according to claim 1 in which Ar is

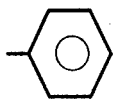

and R and R' are each hydrogen.

4. The p-terphenylene-dicarboxylic acid according to claim 1 in which Ar is

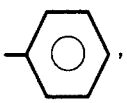

R is hydrogen and R' is

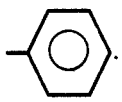

5. The p-terphenylene-dicarboxylic acid according to claim 1 in which Ar is

and R and R' are each

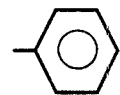

6. The p-terphenylene-dicarboxylic acid according to claim 1 in which Ar is

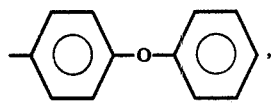

R is hydrogen and R' is

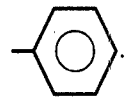

7. A p-terphenylene-dicarboxylic acid having the following structural formula:

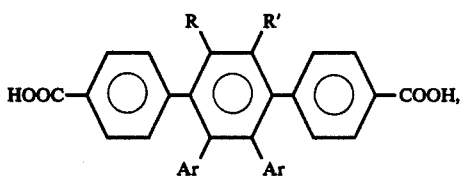

wherein Ar is

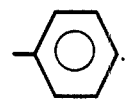

and R and R' are individually selected from the group consisting of hydrogen and

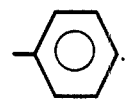

* * * * *